(12) United States Patent
Lundquist

(10) Patent No.: US 6,730,816 B2
(45) Date of Patent: May 4, 2004

(54) HIGH PRODUCTIVITY BISPHENOL-A CATALYST

(75) Inventor: Eric Gustave Lundquist, North Wales, PA (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 09/995,186

(22) Filed: Nov. 27, 2001

(65) Prior Publication Data

US 2002/0123534 A1 Sep. 5, 2002

Related U.S. Application Data

(60) Provisional application No. 60/259,430, filed on Dec. 29, 2000.

(51) Int. Cl.⁷ ............................ C07C 39/12; C07C 39/16
(52) U.S. Cl. .......................... 568/727; 521/33; 568/728
(58) Field of Search ................................. 568/727, 728; 521/33

(56) References Cited

U.S. PATENT DOCUMENTS

| 4,177,331 A | 12/1979 | Amick ........................ 521/33 |
| 5,233,096 A | 8/1993 | Lundquist ................... 568/727 |
| 5,616,622 A | 4/1997 | Harris et al. .................. 521/33 |

*Primary Examiner*—Judy M. Reddick
(74) *Attorney, Agent, or Firm*—Witold Andrew Ziar; Stephen E. Johnson

(57) ABSTRACT

A high productivity catalyst for bisphenol-A has been discovered which comprises strongly acidic cation-exchange resin spheres produced from a polystyrene/divinylbenzene (PS/DVB) copolymer sulfonated under conditions to introduce sulfone cross-linking. Surprisingly, the sulfone cross-linking improves the resistance to deformation but does not have a negative effect on the activity and selectivity of the catalyst in bisphenol-A production.

9 Claims, No Drawings

HIGH PRODUCTIVITY BISPHENOL-A CATALYST

CROSS REFERENCE TO RELATED PATENT APPLICATIONS

This is a non-provisional application of prior U.S. provisional application serial No. 60/259,430 filed Dec. 29, 2000.

The present invention relates to a catalyst composition for significantly increasing the productivity of fixed-bed reactors in the production of bisphenol-A.

Industrial production of bisphenol-A (BPA) currently involves a process whereby a mixture of excess phenol and acetone is passed through a cylindrical fixed-bed reactor filled with divinyl benzene cross-linked sulfonated polystyrene ion exchange resin catalyst. The direction of flow of the mixture may be either downwards or upwards as required by reactor design. Each feed direction has its own advantages and disadvantages. Typically, the flow of the viscous reactant mixture is down-flow. Where the feed directions is downwards, the pressure drop through the sulfonic acid resin catalyst bed is a major problem limiting the throughput of reactants and products, which ultimately limits the production of bisphenol-A. The pressure drop is caused by a variety of factors, including the viscosity and density of both reactants and products, particle size and particle size distribution of catalyst and the compressibility of the catalyst. The compressibility of the sulfonic acid catalyst appears to be an important factor relating to the pressure drop level. The spherical catalyst particles can be compressed/deformed under pressure into a variety of non-spherical or lenticular shapes and a loss in bed void fraction, leading to an exponential reduction in throughput. Moreover, compression of the catalyst bed under pressure can promote the formation of flow channels so that flow through the reactor is not uniform. As a result, the quantity of catalyst used as a whole may not be fully utilized.

An optimized catalyst system for the synthesis of bisphenol-A has been disclosed by Berg et. al. in U.S. Pat. No. 5,395,857. Berg et. al. disclose sulfonic acid catalyst beds for increasing the volume/time yield of fixed-bed reactors in the production of bisphenol-A from phenol and acetone in cylindrical fixed-bed reactors filled with gel-form or macroporous sulfonic acid ion exchange resin catalysts, characterized in that the lower layer of the bed consists of a resin having a low degree of cross-linking (=2%) and makes up 75 to 85% by volume of the bed as a whole and the upper layer of the bed, which makes up 15 to 25% by volume, consisting either of a resin having a higher degree of cross-linking (=2% to =4%), in which 1 to 25 mole % of the sulfonic acid groups may be covered with species containing alkyl-SH units (ionic fixing) or of a resin having a low degree of cross-linking (=2%), in which 1 to 25 mole % of the sulfonic acid groups are covered with species containing alkyl-SH units (ionic fixing).

Yet another catalyst system for the synthesis of bisphenol-A has been disclosed by Kissinger et al. in the International Publication No. WO 00/50372A1. Kissinger et al. discloses an improved process for the production of bisphenol-A employing a catalytic ion exchange resin bed in which the lower portion of the bed is filled with a resin which has a higher degree of crosslinking than the upper layer and the upper portion of the bed is filled with an unmodified resin having a low degree of crosslinking or a resin having a low degree of crosslinking in which 1 to 35 mol % of the sulfonic acid groups are covered with species containing alkyl-SH groups by ionic fixing.

A reactor system for bisphenol-A is also disclosed in International Publication No. WO 97/34688 in which the reactor is operated in an upflow mode with a fixed bed catalyst and randomly distributed reactor packing, employing lightly cross-linked ion exchange resin catalysts, typically containing no greater than 2 to 4% divinylbenzene cross-linking.

It is preferred that in both reactor systems, the catalysts are sulfonated aromatic resins comprising cross-linked polymers, typically polystyrene/divinyl benzene (PS/DVB) copolymers, having a plurality of pendant sulfonic acid groups. In both types of reactor systems, when the catalyst contains 1 to 3% cross-linking, catalyst compression and the resulting pressure drop becomes more limiting than the acetone reaction rate. The compressibility of the catalyst particles can be decreased by increasing the amount of cross-linking material (divinyl benzene) used in the copolymerization. However, as taught in U.S. Pat. No. 5,395,857, increasing the amount of cross-linking material decreases the reactivity and selectivity of the bisphenol-A catalyst to produce BPA.

A process has been discovered in which the pressure drop in the industrial production of bisphenol-A from acetone and phenol in a cylindrical fixed-bed reactor filled with sulfonic acid ion exchange resin catalysts in large quantities can be significantly reduced. According to the present invention, catalyst compressibility can be substantially decreased by cross-linking the PS/DVB copolymer with sulfone bridges during the sulfonation process. Surprisingly, the sulfone cross-linking does not have a negative effect on the activity and selectivity of the catalyst in bisphenol-A production. The sulfonation process used to introduce sulfone cross-linking has also been found to introduce additional sulfonic acid groups so that the average styrene aromatic ring contains more than one sulfonic acid group. The catalysts used in the process of the present invention provide an unexpected combination of desired performance properties in the synthesis of bisphenol A: reactivity, selectivity, compressibility and hydraulic characteristics.

According to present invention, a high productivity catalyst for bisphenol-A has been discovered which comprises strongly acidic cation-exchange resin spheres produced from a polystyrene/divinylbenzene (PS/DVB) copolymer sulfonated under conditions to introduce sulfone cross-linking. Surprisingly, the sulfone cross-linking improves the resistance to deformation but does not have a negative effect on the activity and selectivity of the catalyst in bisphenol-A production. The catalysts used in the process of the present invention provide an unexpected combination of desired performance properties in the synthesis of bisphenol A: reactivity, selectivity, compressibility and hydraulic The bisphenol-A catalyst of the present invention is characterized in that the spherical catalyst particles substantially resist deformation under pressure as compared to currently known bisphenol-A catalysts and posses higher reactivity as compared to currently known bisphenol-A catalysts.

According to present invention, a high productivity catalyst for bisphenol-A has been discovered which comprises strongly acidic cation-exchange resin spheres produced from a polystyrene/divinyl benzene (PS/DVB) copolymer sulfonated under conditions to introduce sulfone cross-linking.

The spherical bisphenol-A catalyst particles were formed by suspending a mixture of styrene and divinylbenzene monomers and initiators in an aqueous liquid, and subsequently polymerizing the mixture to produce spherical copolymer beads, that when sulfonated to introduce sulfonic acid groups and sulfone crosslinking give a catalyst of surprisingly high reaction rates and low deformation when used to catalyze the conversion of phenol with acetone to bisphenol-A.

The process by which the catalyst is made, comprises suspending a mixture of styrene and divinylbenzene monomers and a free-radical polymerization initiator into an aqueous suspending medium that is agitated to form monomer droplets, heating the droplets to a temperature above the activation temperature of the polymerization initiator until the droplets polymerize, separating the resulting polymer beads from the suspending medium, drying the beads, functionalizing the beads with strongly acidic cation-exchange groups and sulfone cross-links. The process of making such types of ion exchange resin catalysts of uniform particle size without sulfone cross-linking is disclosed by Lundquist in U.S. Pat. No. 5,233,096.

The monounsaturated vinyl aromatic monomers useful in preparing the cross-linked copolymer beads of the present invention include styrene and substituted styrenes such as α-methyl styrene, vinyltoluene, ethyl vinyl benzene, vinyl naphthalene and the like. The polyvinylaromatic monomers include aromatic cross-linking monomers such as divinyl benzene, divinyl toluene, trivinyl benzene, divinyl chloro benzene, diallyl phthalate, divinyl naphthalene, divinyl xylene, divinyl ethyl benzene, trivinyl naphthalene and polyvinyl anthracenes; and aliphatic cross-linking monomers such as di- and polyacrylates and methacrylates exemplified by trimethylolpropane trimethacrylate, ethylene glycol dimethacrylate, ethylene glycol diacrylate, neopentyl glycol dimethacrylate and pentaerythritol tetra- and trimethacrylates, and trivinyl cyclohexane. The cross-linking monomer is preferably present at levels from about 0.1% to about 20 weight percent of the total monomer, and more preferably from about 1% to about 10 weight percent of the total monomer. Preferred cross-linking monomers are aromatic cross-linking monomers, and particularly preferred is divinyl benzene.

The jetting suspension-polymerization process useful for forming the uniform cross-linked copolymer beads of the present invention is exemplified by, but not limited to, the process disclosed by Koestler et al. in U.S. Pat. No. 3,922,255. In that process, a minimal solubility of the monomers in the aqueous suspending medium is important. Solubility can be decreased by adding an electrolyte to the aqueous suspending medium. The jetting process produces monomer droplets in the suspending medium whose average diameter for the droplet population is preferably varied over the range from about 20 μm to about 1 mm, and the resulting copolymer beads may be produced with an average diameter for the bead population which varies over the same range. The jetting suspension-polymerization process produces a droplet size distribution that is narrow, resulting in uniformly sized droplets and uniformly sized copolymer beads. Other processes which form uniformly sized copolymer beads by jetting monomer into an aqueous suspending liquid may be used, as for example that disclosed by Timm et al. in U.S. Pat. No. 4,623,706, which uses a vibrating orifice to jet the monomer into the suspending medium. The suspending medium preferably moves with relation to the jetting orifice or orifices, and the monomer droplets may either by polymerized in the vicinity of the orifices by jetting the monomer into the suspending medium at the polymerization temperature, or they may be polymerized in a different zone of the polymerization apparatus by causing the moving suspending medium to carrying them into a heated polymerization zone. Alternatively, the uniform jetted monomer beads may be encapsulated with stable shells and polymerized as taught by Lange et al. in U.S. Pat. No. 4,427,794.

The polymerized beads may be separated from the suspension medium by gravity, by centrifugal flow, by hydraulic separation or by filtration.

The monomers may be jetted by themselves, or mixed with inert liquids or prepolymers which are dissolved in the monomers or formed by prepolymerization of the monomers, or by a combination of both methods. The preferred jetting rate produces a ratio of suspending medium to monomer of from about 1.5:1 to about 10:1, and more preferably from about 2:1 to about 5:1. The monomer may be jetted into the suspending medium at a temperature about the activation temperature of the free-radical polymerization initiator described below, which will cause polymerization to begin almost immediately, or the medium may be below the activation temperature, but preferably above about 15° C., and be heated subsequently, after flowing into a heating zone; this will permit the monomer droplets to stabilize before polymerization begins.

All commonly used stabilizers, especially gelatin, starch, carboxymethylcellulose, polyacrylic acids, polyvinyl alcohol; or water-insoluble inorganic stabilizers in particulate form, such as bentonite, magnesium hydroxide and the like; or combinations of such stabilizers may be used to stabilize the monomer droplets in this or other jetting suspension-polymerization processes.

Free-radical polymerization initiators are preferred to initiate polymerization of the monomer droplets suspended in the suspending medium. Preferred free-radical polymerization initiators are oil-soluble initiators which are dissolved in the monomer, such as benzoyl peroxide, lauroyl peroxide, t-butyl peroctoate, t-butyl peroxy benzoate, t-butyl peroxy pivalate, t-butylperoxy-2-ethylhexanoate, bis(4-t-butyl cyclohexyl) peroxy dicarbonate and the like; and azo compounds such as azo bis(isobutrylonitrile), azo bis (dimethyl valeronitrile) and the like. The polymerization temperature, that is, the temperature at which the suspending medium is held during polymerization of the monomer droplets, and the polymerization initiator are interdependent in that the temperature must be high enough to break the chosen initiator down in to an adequate number of free radicals to initiate and sustain polymerization, that is, it must be above the activation temperature of the initiator. Preferred polymerization temperatures are from about 40° C. to about 100° C., and more preferably from about 50° C. to about 90° C., and the free-radical initiator is chosen so that it has an activation temperature below the polymerization temperature.

According to the present invention, spherical particles of the bisphenol-A catalyst were obtained by sulfonating a styrene/divinylbenzene copolymer under conditions to introduce sulfonic acid groups and sulfone cross-linking. Surprisingly, the sulfone cross-linking prevents bead deformation and yet does not have a negative effect on the activity and selectivity of the catalyst in bisphenol-A production. More specifically, the catalyst resins of the present invention involve strong acid, sulfone cross-linked PS/DVB ion exchange resins having a relatively low degree of divinyl benzene cross-linking, from 0.5% to 5.0%. In a preferred embodiment, the invention is directed to uniformly sized beads of a strong acid, sulfone cross-linked PS/DVB ion exchange resin catalyst produced by the cross-linking and functionalization of a spherical PS/DVB copolymer bead of uniform size.

According to the present invention, a novel class of sulfone cross-linked PS/DVB ion exchange resin catalysts having excellent physical stability and high capacity for conversion of phenol and acetone to bisphenol-A. The resins are, preferably of uniform size, avoiding the requirement for later separation of off-size particles. By the method of the invention, PS/DVB copolymers may be both sulfone cross-linked and functionalized simultaneously with the sulfonating reagent mixture to afford catalysts of the present invention. Sulfone cross-linked polystyrene materials and the process to produce such materials are disclosed by Amick in U.S. Pat. No. 4,177,331. The process described in U.S. Pat. No. 4,177,331 produced a sulfone cross-linked linear polystyrene resin that had excellent physical stability and high capacity for ion exchange. A method for producing sulfone cross-linked materials from seeded, cross-linked polystyrene copolymers is disclosed by Harris, et. al. in U.S. Pat. No. 5,616,622. The oxidative stability of seeded cation exchange resins could be increased by the introduction of secondary cross-linking such as sulfone cross-links.

Sulfonation of PS/DVB by the process of the present invention accomplishes not only sulfone cross-linking of the polymer but yields catalysts containing polysulfonation in which the aromatic ring contains more than one sulfonic acid group per ring. Sulfonated cross-linked vinyl benzene polymers containing more than one sulfonic acid group per aromatic nucleus and a process of producing such sulfonated polymers are disclosed by Corte et. al. in U.S. Pat. No. 3,158,583.

It was found that granules or beads of PS/DVB copolymer may be sulfone cross-linked and functionalized with a particular sulfonating reagent mixture in an efficient and controllable manner. The reagents useful by the process of the invention include various combinations of chlorosulfonic acid, sulfur trioxide, sulfuric acid, and boron compound such as boric acid and boron oxide. The combinations of sulfonating reagents and boron compounds most desirable for introducing sulfone cross-linking to cross-linking PS/DVB copolymers are as follows: sulfuric acid/sulfur trioxide, chlorosulfonic acid/sulfur trioxide, chlorosulfonic-sulfur trioxide/boron compound, chlorosulfonic acid/sulfuric acid/boron compound, sulfur-trioxide/sulfuric acid/boron compound.

The sulfonation of aromatic compounds, either monomeric or polymeric, taught heretofore with chlorosulfonic acid or sulfur trioxide inherently lead to the formation of some sulfone linkages It is known that sulfone bridges result from the electrophilic attack of "pyrosulfonic acid" intermediates upon unreacted aromatic rings; these intermediates are, in turn, formed by the reaction of a sulfonic acid with $SO_3$ (W. H. C. Ruegeberg, T. W. Sauls, and S. L. Norwood, J. Org. Chem., 20, 455, 1955). We have found that by adjusting the concentration of the sulfuric acid/$SO_3$ mixture, that the number of sulfone bridges can be controlled. It is preferred that sulfuric acid/$SO_3$ mixtures, also known as oleum, having acid concentrations of between 101.0% and 104.5% (20% oleum contains 20% by weight of $SO_3$ in 100% sulfuric acid, for a final acid concentration of 104.5%) be used as the sulfonating agents to introduce both sulfone bridging groups and at least one sulfonic acid group per aromatic nucleus.

The number of sulfone bridges contained in the catalyst of the present invention can be determined by subtracting the millimoles of sulfonic acid groups per gram of dry catalyst, determined by titration of the sulfonic acid groups, from the millimoles of total sulfur determined by elemental analysis. The difference is the millimoles of sulfone bridges per gram of dry catalyst. In theory, if each of the aromatic rings is sulfonated, the low cross-linked cation exchange resin should have a capacity of approximately 5.1 millimoles acid groups per gram of dry resin and an elemental analysis of sulfur of 16.2 weight percent. If a catalyst was found to have a capacity of 5.7 millimoles acid groups per gram of dry catalyst and a sulfur elemental analysis of 19%, then in one gram of dry catalyst 0.6 millimoles of the aromatic rings have two sulfonic acid groups and the catalyst has 0.2 millmoles of sulfone bridging groups. The catalyst contains 0.1 to 1.0 millimole sulfone groups per gram dry catalyst, and has an acid capacity of 4.0 to 6.0 millimole sulfonic acid groups per gram dry catalyst. In a preferred embodiment, the catalyst contains 1 to 6 percent of divinylbenzene crosslinking, more preferably 4.5 to 6 and most preferably 5 to 6 and the catalyst contains 0.1 to 0.8 millimoles of sulfonic acid groups per gram of dry catalyst, more preferably 0.2 to 0.5 millimole of sulfone groups per gram of dry catalyst.

The catalyst according to the present invention for the synthesis of bisphenol A represents an unexpected combination of reactivity, selectivity, compressibility and hydraulic performance for the synthesis of bisphenol-A. A preferred catalyst of the present invention comprises a copolymer of between 1.0 and 10.0% divinylbenzene cross-linking, preferably between 1 and 5% divinylbenzene crosslinking, sulfonated to a dry weight capacity of greater than 4.0 mmol/g and preferably greater than 5.0 mmol/g, possessing 0.1 to 1.0, preferably 0.1 to 0.8 and more preferably 0.2 to 0.5 mmol/g of sulfone bridging groups. In a separate embodiment, the catalyst further comprises 1 to 35 mol % of the sulfonic acid groups containing an ionically attached thiol promoter.

The reactions catalyzed by the sulfone-bridged, strongly acidic cation-exchange resin beads of the present invention are those reactions that are catalyzed by the presence of strong acids, and include, but are not limited to, condensation reactions, for example the condensation of phenols with ketones or aldehydes to produce bisphenols. A preferred reaction which is catalyzed by the strongly acidic ion-exchange resin beads of the present invention is the reaction of phenol with acetone to produce bisphenol A. More preferred is that reaction in which phenol and acetone are combined in a molar ratio of from about 20:1 to about 2:1 and the combination is contacted, at from about 40° C. to about 100° C., with from about 1 to about 40 weight percent (based on the weight of phenol and acetone) of the strongly acidic ion-exchange resin beads of the present invention, optionally in the presence of from about 0.1 to about 40 weight percent (based on the weight of phenol and acetone) of a mercaptan reaction promoter, preferably ethanethiol, 3-mercaptopropionic acid, aminoethane thiol or dimethyl thiazolidine. Aminothiol promoters such as aminoethane thiol and dimethyl thiazolidine can be ionically attached to the ion exchange resin of the present invention. The attachment of ionic promoters is described in U.S. Pat. No. 3,394,089.

Due to the size of fixed bed BPA reactors and the viscosity of the BPA reaction stream, BPA production rates are greatly affected by pressure drop. As such, catalyst factors such as particle size, particle uniformity and compressibility need to be understood in order to produce BPA at acceptable rates and allow for instantaneous production increases to meet market demand. The particle size and uniformity of the BPA catalysts can be tightly controlled as disclosed by Lundquist in U.S. Pat. No. 5,233,096. The compression of the BPA catalyst bead is not well understood but can be tested by measuring the deformation of the catalyst bead under a gradual increase in force. The resulting measurement known as the compression modulus of the catalyst was determined in a phenol swollen state using a Chatillion instrument with the compression modulus being the slope of the line measuring the initial deformation of the bead up to a force of 200 grams/bead.

The use of the strongly acidic cation exchange resin beads containing sulfone cross-linking for the condensation of phenols with aldehydes or ketones allows for higher production rates of BPA by increasing both catalytic and hydraulic performance. The increased hydraulic performance is achieved by the introduction of sulfone cross-linking that make the bead more resistant to deformation and thus capable of withstanding higher reactor flow rates. Surprisingly, equivalent or increased catalyst activity for the production of bisphenol-A are achieved even at increased cross-linking levels. Without wishing to be bound by theory, it is believed that the resistance to deformation and higher conversion rates result from the unanticipated interaction of the phenol acetone reaction mixture with the sulfone cross-linked polysulfonated resin catalyst structure. The ability to produce more bisphenol product in a given time, which is afforded by a higher reaction rate and flow rate in such processes, is an advantage that is readily apparent to those skilled in the art.

EXPERIMENTIAL EXAMPLES

In the following examples, all reagents used are of good commercial quality, unless otherwise indicated, and all percentages and ratios given herein are by weight unless otherwise indicated.

Example 1

Example illustrates the typical preparation of the jetted PS/DVB copolymer beads useful in making the sulfone-bridged strongly acidic, cation exchange resin beads of the present invention.

An aqueous suspending medium was prepared containing 0.55% of Acrysol A-3 polyacrylic acid dispersant, 0.2% sodium hydroxide, 0.39% boric acid, 0.04% gelatin and having a pH of between 8.5 and 8.7. A monomer solution was prepared containing 3.6% commercial divinyl benzene (containing 55% pure divinyl benzene and 45% ethyl vinyl benzene), 95.8% styrene 0.3% benzoyl peroxide and 0.3% bis(4-t-butylcyclohexyl) peroxy dicarbonate. The monomer mixture was jetted through vibrating jetting orifices 450 µm in diameter, at a rate of 145 kg/hr, into a stream of the suspending medium moving at a rate of 386 liter/hr. This dispersion was conveyed by the flow of suspending medium to a gelling column held at 63° C. The flow produced a residence time of 3.5 hours in the gelling column, and the conversion of monomer to copolymer during this time was 25%. The copolymer was separated from the aqueous phase, which was recycled. The copolymer was then held in a finishing kettle for 4 hours a 65° C., then transferred to a final finishing kettle and held at 80° C. for 1.5 hours, heated to 92° C., and held at that temperature for 1 hour. The finished 2.0% divinylbenzene cross-linked polystyrene copolymer was washed with water and air dried.

Example 2

Example 2 used the process of example 1 to produce a 3.5% divinyl benzene cross-linked copolymer.

Example 3

Example 3 used the process of example 1 to produce a 4.5% divinyl benzene cross-linked copolymer.

Example 4

Catalyst A

In a one liter round bottom flask containing 75 g of copolymer from Example 1 was charged 1000 g of 96% sulfuric acid and 50 g of ethylene dichloride (EDC). This mixture was heated to 125 C. over 1 hour and held at that temperature for 2 hours to remove the EDC and then cooled to 110 C. The sulfonated resin was hydrated at a temperature between 110 C. and 60 C. by consecutive additions of diluted acid and removal of the resulting diluted acid until less than 5% acid remained. The catalyst was washed with 2×500 ml of DI water and packed out. The properties of catalyst A are presented in Table 1.

Example 5

Catalyst B

In a one liter round bottom flask containing 75 g of copolymer from Example 1 was charged 1200 g of 102.5% sulfuric acid. This mixture was heated to 120 C. over 1 hour and held at that temperature for 2 hours and then cooled to 110 C. The sulfonated resin was hydrated at a temperature between 110 C. and 60 C. by consecutive additions of diluted acid and removal of the resulting diluted acid until less than 5% acid remained. The catalyst was washed with 2×500 ml of DI water and packed out. The properties of catalyst B are presented in table 1.

Example 6

Catalyst C

In a one liter round bottom flask containing 75 g of copolymer from Example 1 was charged 1000 g of 20% oleum (104.5% sulfuric acid). This mixture was heated to 120 C. over one hour, held at that temperature for 2 hours and then cooled to 120 C. The sulfonated resin was hydrated at a temperature between 100 C. and 60 C. by consecutive additions of diluted acid and removal of the resulting diluted acid until less than 5% acid remained. The catalyst was washed with 2×500 ml of DI water and packed out. The properties of catalyst C are presented in Table 1.

Example 7

Catalyst D

In a one liter round bottom flask containing 100 g of copolymer from Example 2 was charged 900 g of 96% sulfuric acid and 40 g of ethylene dichloride (EDC). This mixture was heated to 125 C. over 1 hour and held at that temperature for 2 hours to remove the EDC and then cooled to 110 C. The sulfonated resin was hydrated at a temperature between 110 C. and 60 C. by consecutive additions of diluted acid and removal of the resulting diluted acid until less than 5% acid remained. The catalyst was washed with 2×500 ml of DI water and packed out. The properties of catalyst D are presented in table 1.

Example 8
Catalyst E

In a one liter round bottom flask containing 100 g of copolymer from Example 2 was charged 850 g of 20% oleum (104.5% sulfuric acid). This mixture was heated to 120 C., held at that temperature for 2 hours and then cooled to 120 C. The sulfonated resin was hydrated at a temperature between 110 C. and 60 C. by consecutive additions of diluted acid and removal of the resulting diluted acid until less than 5% acid remained. The catalyst was washed with 2×500 ml of DI water and packed out. The properties of catalyst E are presented in table 1.

Example 9
Catalyst F

In a one liter round bottom flask containing 100 g of copolymer from Example 3 was charged 800 g of 96% sulfuric acid and 40 g of ethylene dichloride (EDC). This mixture was heated to 125 C. over 1 hour and held at that temperature for 2 hours to remove the EDC and then cooled to 110 C. The sulfonated resin was hydrated at a temperature between 110 C. and 60 C. by consecutive additions of diluted acid and removal of the resulting diluted acid until less than 5% acid remained. The catalyst was washed with 2×500 ml of DI water and packed out. The properties of catalyst F are presented in Table 1.

The catalytic activity of the ion exchange resin catalysts for BPA synthesis was determined using a CSTR reactor with a reaction mixture containing a phenol to acetone molar ratio of 10:1 and a temperature of 70 C.

Promoted catalysts were prepared by neutralizing 17% of the acidic sites with aminethanethiol promoter. Composition of the reaction mixture was determined by HPLC using a 250×4 mm column filled with Nucleosil C18 and 66% volume methanol in water as the mobile phase. The flow rate was 0.6 ml/minute with photometric detection at the wavelength 290 nm. Acetone conversion was computed from the determined phenol/BPA ratio and the known phenol/acetone ratio in the starting reaction mixture. The initial reaction rates for for both promoted and non promoted catalysts are presented in Table 2.

Example 11

This example illustrates the resistance of deformation of the strongly acidic cation exchange resins of the present invention under a force of up to 200 gram per bead.

The compression modulus of the catalyst was measured in phenol swollen state using a Chatillion instrument with the compression modulus being the slope of the line measuring the initial deformation of the bead up to a force of 200 grams/bead. The higher the compression modulus value, the more resistant the material is to deformation under an applied force. The results are presented in Table 2.

TABLE 1

Catalyst Properties

| Catalyst | A | B | C | D | E | F |
|---|---|---|---|---|---|---|
| % DVB | 2% | 2% | 2% | 3.5% | 3.5% | 4.5% |
| Appearance | smooth, noncracked beads | smooth, noncracked beads | smooth, noncracked beads | smooth, noncracked beads | smooth, noncracked beads | smooth, noncracked beads |
| MHC | 82.4% | 77% | 74.2% | 71.5% | 66.2% | 65% |
| Acid Wt. Cap. | 5.08 mmol/g | 5.67 mmol/g | 5.63 mmol/g | 5.09 mmol/g | 5.53 mmol/g | 5.09 mmol/g |
| Acid Vol. Cap. | 0.63 mmol/ml | 1.09 mmol/ml | 0.94 mmol/ml | 1.11 mmol/ml | 1.44 mmol/ml | 1.32 mmol/ml |
| % Sulfur | 16.25 | 18.86 | 19.47 | 16.28 | 19.02 | 16.2 |
| mmol sulfone bridging groups | 0 | 3.7 | 7.5 | 0 | 10.8 | 0 |

Example 10

This example illustrates the catalytic activity of the strongly acidic cation exchange resins of the present invention in catalyzing the condensation of phenol and acetone.

TABLE 2

| Catalyst | A | B | C | D | E | F |
|---|---|---|---|---|---|---|
| % DVB | 2% | 2% | 2% | 3.5% | 3.5% | 4.5% |
| sulfone bridging groups | 0 | 0.22 mmol/g | 0.45 mmol/g | 0 | 0.41 mmol/g | 0 |
| Compression modulus | 472 | 743 | 1992 | 700 | 3265 | 740 |
| Unpromoted initial reaction rate | 6.4 mmol/g hr | 6.7 mmol/g hr | 6.1 mmol/g hr | 6.6 mmol/g hr | 7.9 mmol/g hr | 2.6 mmol/g hr |
| Promoted initial reaction rate | 47.4 mmol/g hr | 64.2 mmol/g hr | 34.1 mmol/g hr | 20.4 mmol/g hr | 22.6 mmol/g hr | 18.1 mmol/g hr |

I claim:

1. A process for catalyzing condensation reactions between reactants selected from phenols and aldehydes or ketones to produce one or more bisphenols, which comprises contacting the reactants with a sulfone cross-linked ion exchange resin catalyst having improved resistance to deformation under pressure, the catalyst comprising polymerized monomer units of (a) from 0.1 to 10 percent by weight of one or more polyvinylaromatic monomers and (b) from 90 to 99.9 percent by weight of one or more monounsaturated vinylaromatic monomers; and from 0.1 to 1.0 millimole sulfone bridges per grain dry catalyst.

2. The process according to claim 1, wherein at least one bisphenol is bisphenol-A.

3. The process according to claim 1, wherein the catalyst is present at from about 1% to 40% by weight, based on total weight of the reactants.

4. The process according to claim 1, wherein the ion exchange resin catalyst is in the form of spherical beads prepared from a jetted, suspension polymerized polystyrene divinylbenzene copolymer.

5. The process according to claim 1, wherein the ketone is acetone and the phenol and acetone are present in a ratio of from about 20:1 to about 2:1.

6. The process according to claim 1, wherein the reactants contact the catalyst resin at a temperature from about 40° C. to about 100° C.

7. The process according to claim 1, wherein the catalyst further comprises 1% to 35% by weight of sulfonic acid groups containing an ionically attached thiol promoter.

8. A process for preparing bisphenol-A from phenol and acetone in a fixed bed rector comprising the step of contacting a mixture of phenol and acetone with a sulfone cross-linked ion exchange resin catalyst prepared from jetted suspension polymerized polystyrene divinylbenzene copolymer beads having from 0.1 to 1.0 millimole sulfone bridges per gram dry catalyst and improved resistance to deformation under pressure.

9. The process according to claim 1, wherein the condensation reaction is performed in a fixed bed reactor either alone or in combination with a catalyst of a different cross-linking level.

* * * * *